United States Patent
Koide

(10) Patent No.: US 8,030,448 B2
(45) Date of Patent: Oct. 4, 2011

(54) POLYPEPTIDE HAVING COLLAGEN-LIKE STRUCTURE

(75) Inventor: Takaki Koide, Nigata (JP)

(73) Assignees: Techno Network Shikoku Co., Ltd., Kagawa (JP); Nippi, Incorporated, Tokyo (JP)

(*) Notice: Subject to any disclaimer, the term of this patent is extended or adjusted under 35 U.S.C. 154(b) by 836 days.

(21) Appl. No.: 10/589,557

(22) PCT Filed: Feb. 3, 2005

(86) PCT No.: PCT/JP2005/001583
§ 371 (c)(1), (2), (4) Date: Jan. 23, 2007

(87) PCT Pub. No.: WO2005/078085
PCT Pub. Date: Aug. 25, 2005

(65) Prior Publication Data
US 2007/0149764 A1    Jun. 28, 2007

(30) Foreign Application Priority Data
Feb. 16, 2004  (JP) .................................. 2004-038612

(51) Int. Cl.
A61K 38/17   (2006.01)
A61K 38/06   (2006.01)
(52) U.S. Cl. ....................................... 530/331; 530/356
(58) Field of Classification Search ............... 530/356
See application file for complete search history.

(56) References Cited

U.S. PATENT DOCUMENTS
5,973,112 A   10/1999  Raines
6,190,886 B1   2/2001  Hoppe et al.

FOREIGN PATENT DOCUMENTS
JP    10-500298 A     1/1998
WO    WO-95/31540 A1  11/1995
WO    WO-99/10381 A1   3/1999

OTHER PUBLICATIONS

Ottl et al. Disulfide-Bridged Heterotrimeric Collagen Peptides Containing the Collagenase Cleavage Site of Collagen Type I. Synthesis and Conformational Properties. J. Am. Chem. Soc. 1999, 121:653-661.*
Barth et al. The Role of Cystine Knots in Collagen Folding and Stability, Part II. Conformational Properties of (Pro-Hyp-Gly)n Model Trimers with N- and C-Terminal Collagen Type III Cystine Knots. Chem. Eur. J., 2003, 9: 3703-3714.*
Boudko et al. Crystal Structure of Human Type III Collagen Gly991-Gly1032 Cystine Knot-containing Peptide Shows Both ⅞ and ¹⁰⁄₃ Triple Helical Symmetries. 2008, JBC, 283(47):32580-89.*
Ottl et al. Heterotrimeric Collagen Peptides Containing Functional Epitopes. Synthesis of Single-Stranded Collagen Type I Peptides Related to the Collagenase Cleavage Site1. J. Peptide Science, 1999, 5:103-110.*
Koide, T., Designed triple-helical peptides as tools for collagen biochemistry and matrix engineeringPhil. Trans. R. Soc. B, 2007, 362: 1281-91.*
Martin, R. et al. Biopolymers 70, 435-444, 2003.
Fields, GB, Bioorg. Med. Chem. 7, 75-81, 1999.
Koide, Takaki et al., "Synthesis of heterotrimeric collagen models containing Arg residues in Y-positions and analysis of their conformational stability," Bioorganic & Medical Chemistry Letters, 2004, vol. 14, pp. 125-128.
Mechling, Diane E. et al., "The collagen-like peptide (GER)₁₅GPCCG forms pH-dependent covalently linked triple helical trimers," The Journal of Biological Chemistry, May 12, 2000, vol. 275, No. 19, pp. 14532-14536.
Goodman, Murray et al., "Collagen-like triple helices incorporating peptoid residues," J. Am. Chem. Soc., 1996, vol. 118, No. 44, pp. 10928-10929.
Ottl, Johannes et al., "Design and synthesis of heterotimeric collagen peptides with a built-in cystine-knot," FEBS Letters, 1996, vol. 398, pp. 31-36.
Yasui, Norihisa et al., "Collagen-protein interactions mapped by phototriggered thiol introduction," J. Am. Chem. Soc., 2003, vol. 125, pp. 15728-15729.

* cited by examiner

*Primary Examiner* — Suzanne M. Noakes
(74) *Attorney, Agent, or Firm* — Birch, Stewart, Kolasch & Birch, LLP

(57) ABSTRACT

Disclosed is a peptide trimer in which three peptides of the same chain length having a repeating unit as a fundamental structure represented by the formula:

-(-Gly-X-Y-)- wherein X and Y each represent any amino acid residue are tethered to one another such that they are shifted relative to one another in the backbone direction. The peptide trimer is capable of forming a polypeptide having a collagen-like triple helix structure. A method of producing the peptide trimer of the invention and a collagen-like molecular aggregate having a triple helix structure comprised of the peptide trimer unit of the invention are also provided.

17 Claims, 7 Drawing Sheets

OGPOGPOGPOGPOGPCGPOGP (SEQ ID NO: 4)

OGPOGCOGPOGPOGPCGPOGP (SEQ ID NO: 5)

OGPOGCOGPOGPOGPOGPOGP (SEQ ID NO: 6)

FIG. 6

POLYPEPTIDE HAVING COLLAGEN-LIKE STRUCTURE

This application is the National phase application under 35 USC § 371 of PCT International Application No. PCT/JP2005/001583 filed on Feb. 3, 2005, which designated the United States. This application also claims priority under 35 U.S.C. § 119(a) on patent application No. 2004-038612 filed in Japan on Feb. 16, 2004.

TECHNICAL FIELD

The present invention relates to a polypeptide having a collagen-like triple helix structure, and a peptide trimer for producing such a polypeptide, as well as methods of producing such a polypeptide and a peptide trimer.

BACKGROUND ART

Collagen is widely used as a base material for a pharmaceutical product or a cosmetic product, as a biocompatible material for regenerative medicine or drug delivery system, and as a support for tissue culture and the like. Currently available collagen is mainly those obtained by purifying collagen from animals such as pigs and cattle. However, in the case where collagen derived from livestock is applied to humans, a risk of prion infection which may cause BSE has become a problem. Alternatively, collagen derived from plants or fish skin has started to be used, however, it involves a risk of gelatin allergy caused by intake of heterologous collagen. Accordingly, supply of a safe substitute for collagen has been demanded. Recently, construction of genetically engineered human collagen-produced system using various host organisms has been attempted, although it has not come into practical use yet.

Collagen has a structure in which three polypeptide chains form a long triple helix. It is well known that three chemically synthesized peptides having a collagen-like sequence are self-assembling to form the same triple helix structure as collagen, and such structures are used in studies of the structure of natural collagen. Collagen-like polypeptide known in the art include, for example, a polypeptide composed of a repeating unit comprising a peptide unit: [-(Pro-Y-Gly)n-]$_a$ (wherein Y represents Pro or Hyp and n represents an integer of 1 to 20) and a peptide unit, [-(Z)r-]$_b$ (wherein Z represents a peptide chain composed of 1 to 10 amino acid residues and r represents an integer of 1 to 20)(JP-A-2003-321500). Known supramolecules composed of a collagen-like peptide sequence include, for example, a collagen triblock peptide of Martin et al.: (Glu)$_5$(Gly-X-Hyp-Gly-Pro-Hyp)$_6$(Glu)$_5$ (SEQ ID NO: 7) (Martin, R. et al., Biopolymers 70, 435-444, 2003) and a "peptide-amphiphile" of Fields (Fields, G B, Bioorg. Med. Chem. 7, 75-81, 1999).

However, there has been no report of a supramolecule which is formed through the intermolecular formation of complementary triple helix extending the molecule in the direction of triple helix axis.

An object of the present invention is to provide a polypeptide having a collagen-like triple helix structure and a peptide unit for producing such a polypeptide.

DISCLOSURE OF THE INVENTION

The present invention provides a peptide trimer in which three peptides of the same chain length having as a fundamental structure a repeating unit represented by the formula:

-(-Gly-X-Y-)- wherein X and Y each represent any amino acid residue, are tethered to one another such that they are shifted relative to one another in the backbone direction. Preferably, the three peptides are tethered to one another via a disulfide bond.

In another embodiment, the present invention provides a method of producing the peptide trimer of the present invention comprising the steps of:
preparing a first peptide having one Cys residue, a second peptide having two Cys residues, one of which has a protected SH group and a third peptide having one Cys residue;
forming a peptide dimer by linking the first peptide to the second peptide via a disulfide bond;
activating the protected SH of the second peptide by converting the protecting group; and
linking the peptide dimer and the third peptide via a disulfide bond.

In still another embodiment, the present invention provides a molecular aggregate having a triple helix structure comprised of the peptide trimer of the present invention. The present invention further provides a method of producing the molecular aggregate of the present invention comprising the step of holding a solution of the peptide trimer at a temperature between 0 and 40° C. for 1 hour or longer.

BRIEF DESCRIPTION OF THE DRAWINGS

FIG. 6 shows another embodiment of a peptide trimer of the present invention.

PREFERRED EMBODIMENTS OF THE INVENTION

Figure 1:
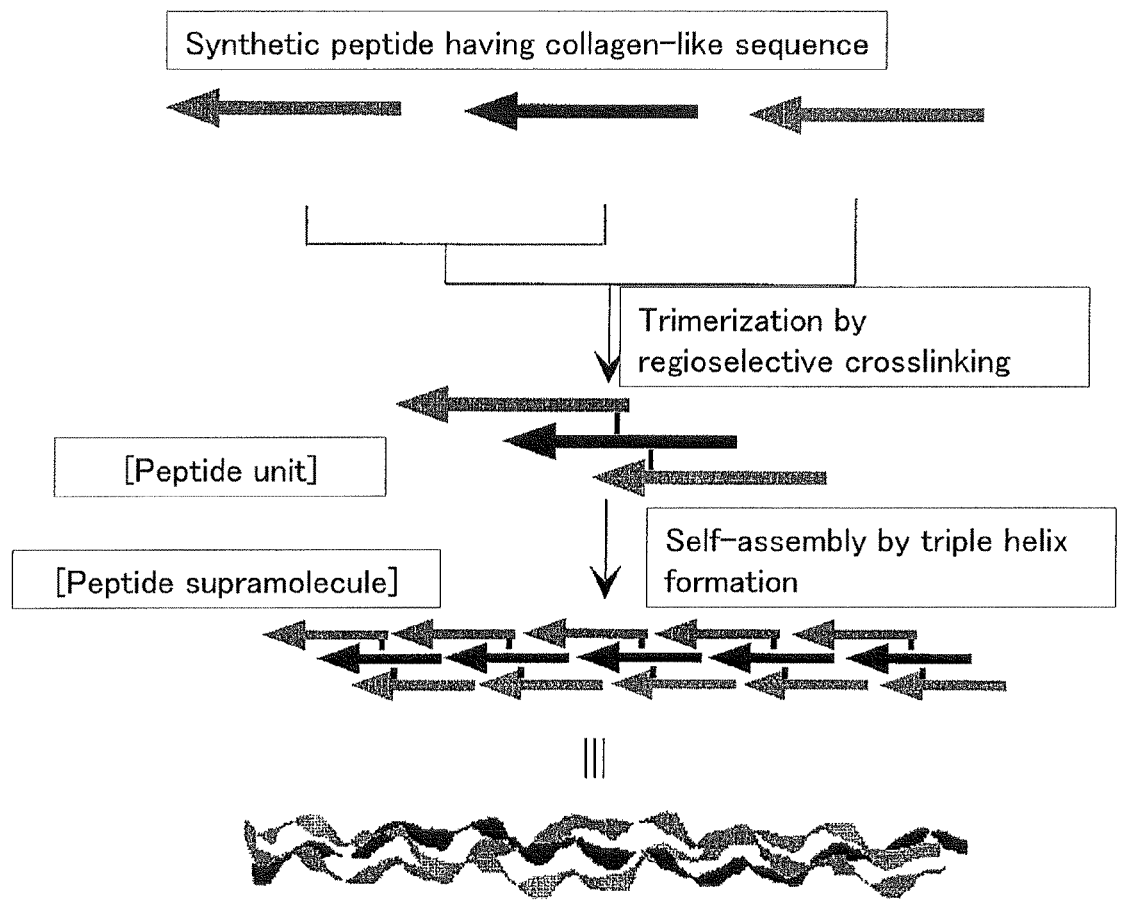
FIG. 1 is a schematic diagram showing a peptide trimer of the present invention and a molecular aggregate having a collagen-like triple helix comprised of the peptide trimer.

The present invention provides a peptide trimer unit formed by trimerization of synthetic peptides having a collagen-like sequence by regioselective crosslink formation. The present invention also provides a method of preparing a supramolecule having a triple helix structure comprising the peptide trimer unit as a constituent unit. The present invention is illustrated in FIG. 1.

Structure of Peptide Trimer Unit

The peptide trimer unit of the present invention has a repeating unit represented by the formula:

-(-Gly-X-Y-)- wherein X and Y each represent any amino acid residue, as a fundamental structure. A polypeptide chain constituting natural collagen has a repeating unit of -(-Gly-Pro-Pro-)- or -(-Gly-Pro-Hyp-)- as its fundamental structure and forms a long left-handed helix. Three polypeptide chains are coiled together and can form an elongated right-handed helix structure with hydrogen bonds between the chains. It is also known that when a solution of peptides with a chain length of about 15 to 30 amino acids having a repeating unit of -(-Gly-Pro-Pro-)- or -(Gly-Pro-Hyp-)- is left stand, they will form a stable triple helix structure similar to that of natural collagen. Such a triple helix structure is as referred to as a "collagen-like structure" herein.

The peptide trimer unit of the present invention is composed of three peptides, each having a fundamental structure composed of a repeating unit of -(-Gly-X-Y-)-, wherein X and Y each represent any amino acid residue. In this formula, X and Y may be a natural amino acid residue or a modified amino acid residue well known in the art, and may be in the L-form or D-form. Preferably the peptide trimer of the present invention is rich in a repeating unit of -(-Gly-Pro-Pro-)- or -(-Gly-Pro-Hyp-)-, which is found in natural collagen. For example, in the whole molecule of the peptide trimer, 30% or more of X is preferably Pro and 30% or more of Y is preferably Pro or Hyp. However, it is known that (Gly-Glu-Arg)n (Mechling, D E. et al., J. Biol. Chem. 275, 14352-14356, 2000), (Gly-Pro-Nleu)n (Nleu=N-isobutylglycine, Goodman, M. et al., J. Am. Chem. Soc. 118, 10928-10929, 1996) or the like also forms a stable triple helix structure, and the peptide trimer of the present invention may have such a repeating unit. By the expression that a peptide "has a fundamental structure composed of a repeating unit of -(-Gly-X-Y-)-", it is not necessary that all the amino acid sequences of the peptides have the repeating unit of -(-Gly-X-Y-)- (i.e., having Gly every three residues), and one or more portions which do not have such a repeating unit may be contained in the peptide sequence. However, in order to form a stable triple helix structure, it is necessary that 80% or more, preferably 90% or more of the amino acid sequences in the peptide trimer molecule has the repeating unit of -(-Gly-X-Y-)-.

Figure 2:
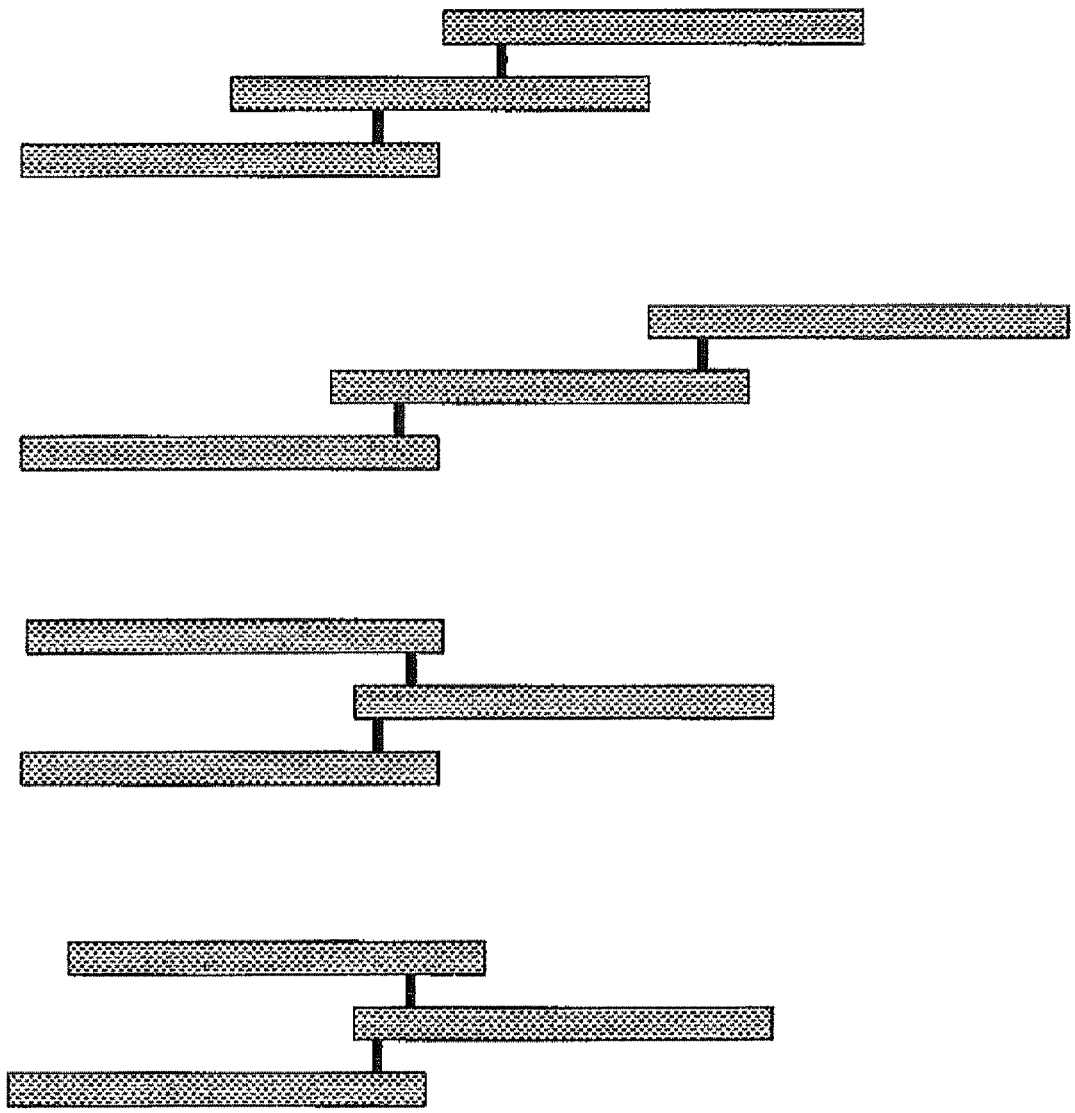
FIG. 2 shows various structures of the peptide trimer of the present invention.

The peptide trimer unit of the present invention has a structure in which three peptides of the same chain length are shifted relative to one another in the backbone (main chain) direction and amino acid side chains are tethered to one another. As used herein, the term "being shifted relative to one another in the backbone direction" means that three peptides are tethered such that all three peptides do not completely overlap with one another. Example of various structures of the trimers are shown in FIG. 2. By tethering three peptides such that they are shifted relative to one another in the backbone direction, three peptides will be prevented from forming a short stable triple helix structure, facilitating the formation of a long triple helix structure containing the peptide trimer as a structural unit. In this structure, a single-stranded region or a double-stranded region in the peptide trimer plays a role as an adhesive for stably holding a plurality of peptide trimers by hydrogen bonds. Therefore, a more preferred structure of the peptide trimer of the present invention, among the structures shown in FIG. 2, is a structure in which a single-stranded region or a double-stranded region is relatively long and a triple-stranded region is relatively short.

Each peptide constituting the peptide trimer unit of the present invention has the same chain length. This enables the peptide trimer to have a stable structure without a gap when they assemble to form a triple helix structure. Each peptide can be synthesized by a known peptide synthesis method, such as a liquid-phase method or a solid-phase method. The chain length is between 10 and 60 amino acid residues, preferably between 15 and 40 residues, more preferably between 20 and 30 residues. When the chain length is shorter, the stability of the formed triple helix structure becomes low, and when the chain length is longer, the cost for peptide synthesis becomes high.

In the peptide trimer unit of the present invention preferably the amino acid side chains of the three peptides are linked to one another. Preferably, the three peptides have Cys residue(s) at an appropriate position, so that the three peptides may be linked to one another via a disulfide bond. Alternatively, the amino acid side chains may be linked via a covalent bond such as an amide bond, a sulfide bond or a Schiff's base bond.

Synthesis Method of Peptide Trimer Unit

The peptide trimer unit of the present invention can be prepared by forming an interchain disulfide bond according to the site directed disulfide bond formation method (Ottl, J. et al., FEBS Lett., 398, 31-36, 1996; Ottl, J. and Moroder, L. J. Am. Chem. Soc. 121, 653-661, 1999; Koide, T. et al., Bioorg. Med. Chem. Lett. 14, 125-128, 2004). Briefly, three peptide chains constituting the peptide trimer are designed such that two peptide chains have one Cys residue and one peptide chain has two Cys residue, and the Cys side chain is linked to the Cys residue of another peptide chain via a disulfide bond.

In the first step of this method, a first peptide having one Cys residue, a second peptide having two Cys residues, one of which has a protected SH group, and a third peptide having one Cys residue are synthesized. Any protecting groups known in the art of peptide synthesis, such as acetoamidomethyl, may be used as the protecting group for the SH group. Then, the first peptide and the second peptide are linked via a disulfide bond to form a peptide dimer. A method of linking SH groups of Cys residues via a disulfide bond is generally known in the art. For example, the SH group on one of the peptide chains is converted to pyridinesulfenyl or nitropyridinesulfenyl moiety and then both peptides are reacted to each other, whereby the Cys residues are linked through a disulfide bond to each other to form a peptide dimer. Then, the protected SH of the second peptide of the peptide dimer is activated by converting the protecting group, and the peptide dimer and the third peptide are linked via a disulfide bond in the same manner as above to obtain the peptide trimer of the present invention. The peptide trimer of the present invention can be purified by column chromatography, HPLC or the like as needed.

Structure and Preparation of Collage-Like Molecular Aggregate

Figure 3:
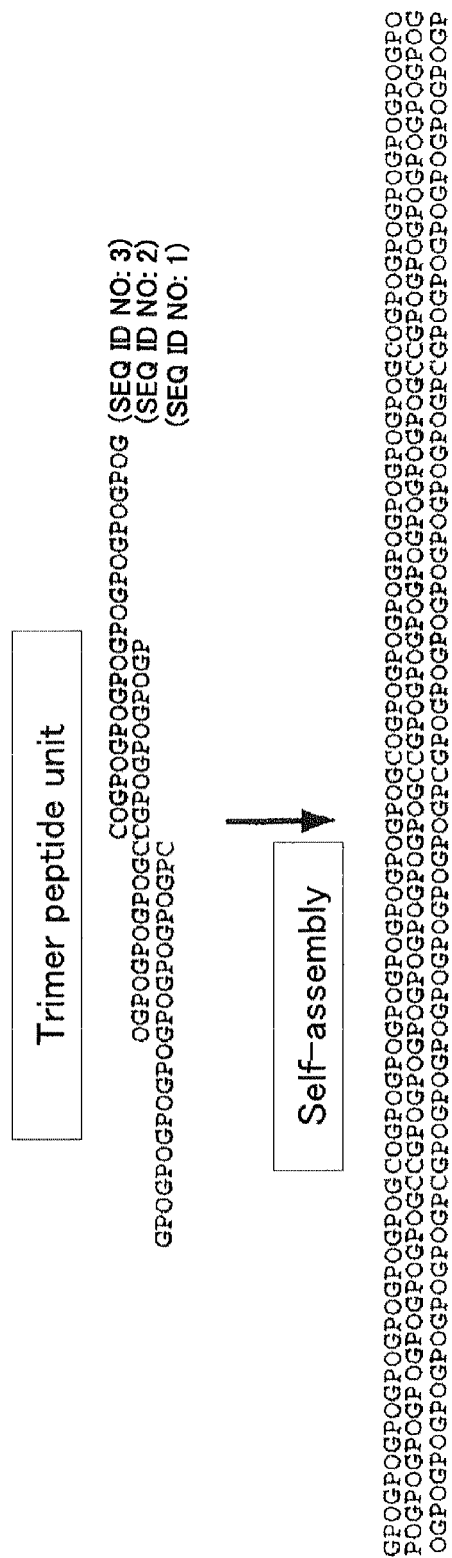
FIG. 3 shows an example of amino acid sequences of a peptide trimer of the present invention and a molecular aggregate comprised of the peptide trimer.

The collagen-like molecular aggregate (supramolecule) of the present invention has the peptide trimer unit of the present invention as a constituent unit and has a fibrous structure having a triple helix structure similar to that of collagen (FIGS. 1 and 3). When a solution of the peptide trimer unit of the present invention is left stand at a lower temperature, complementary self-assembly occurs driven by the formation of a triple helix. For example, the molecular aggregate of the present invention can be formed by holding a solution containing the peptide trimer unit of the present invention at 0 to 40° C., preferably 0 to 10° C. for 1 hour or longer, preferably 12 hours or longer, more preferably 48 hours or longer. An aqueous solution is preferred but an organic solvent can also be used, because the collagen triple helix structure does not contain a hydrophobic core generally found in other proteins.

To determine whether a molecular aggregate having a collagen-like triple helix structure is formed, the structure of the product can be analyzed by measurement of circular dichroism spectrum, measurement of molecular weight, direct observation with an electron microscope, or the like.

The collagen-like molecular aggregate of the present invention may be used in any applications where natural collagen is currently employed. For example, it may be used as a base material for cell culture, in a drug delivery system, and as other biocompatible materials. The collagen-like molecular aggregate of the present invention is advantageous in that it may not lead to risk of prion infection causing BSE or gelatin allergy, both of which are associated with the use of natural collagen.

Furthermore, a specific functional sequence present in natural collagen can be easily incorporated into the collage-like molecular aggregate of the present invention by appropriately designing the peptide trimer according to the present invention. Such a collagen-like molecular aggregate of the present invention will be useful for analyzing the function of natural collagen or developing a functional artificial collagen. It is also possible to prepare a collagen-like supramolecule having a specific function (e.g., a binding ability to a specific protein), for example, a collagen-like supramolecule having a pigment epithelium-derived factor (PEDF) binding sequence identified by the COIDE method (Yasui, N. and Koide, T., J. Am. Chem. Soc. 125, 15728-15729, 2003).

The present invention will be described in more detail with reference to Examples below, however, the present invention is not limited to these Examples.

In the following Examples, all amino acids used were in the L-form. Final products and synthetic intermediates were purified with high performance liquid chromatography. The conditions are as follows.
Column: Cosmosil 5C18-AR
Solvent: A: 0.05% trifluoroacetic acid in water
B: 0.05% trifluoroacetic acid in acetonitrile
Temperature: 42° C.
Elution was carried out be a linear gradient from A to B. The final product and synthetic intermediate were identified by MALDI-TOF MS.

EXAMPLE 1

Synthesis of a Peptide Unit Having Pro-Hyp-Gly Repeats as a Fundamental Sequence (FIG. 3)

1) Construction of Peptide Chains
N-Peptide (SH):
H-Gly-Pro-Hyp-Gly-Pro-Hyp-Gly-Pro-Hyp-Gly-Pro-Hyp-Gly-Pro-Hyp-Gly-Pro-Hyp-Gly-Pro-Hyp-Gly-Pro-Cys (SH)-OH (SEQ ID NO: 1)
M-peptide (Acm, SH):
H-Hyp-Gly-Pro-Hyp-Gly-Pro-Hyp-Gly-Pro-Hyp-Gly-Cys (Acm)-Cys(SH)-Gly-Pro-Hyp-Gly-Pro-Hyp-Gly-Pro-Hyp-Gly-Pro-OH (SEQ ID NO: 2)
C-peptide (SH):
H-Cys(SH)-Hyp-Gly-Pro-Hyp-Gly-Pro-Hyp-Gly-Pro-Hyp-Gly-Pro-Hyp-Gly-Pro-Hyp-Gly-Pro-Hyp-Gly-Pro-Hyp-Gly-OH (SEQ ID NO: 3)

The above three peptide chains were constructed by a standard Fmoc solid-phase synthesis method on a TrtA-PEG resin (Watanabe Chemical Industries, Ltd.). As amino acids with protection of the side chain functional group, Fmoc-Hyp (tBu)-OH, Fmoc-Cys(Acm)-OH and Fmoc-Cys(Trt)-OH were used (abbreviations: Hyp or O: 4-hydroxyproline; Acm: acetoamidomethyl; Trt: trityl).

2) Cleavage of Peptides from Resin and Deprotection
Each peptide-resin (about 0.1 mmol) was mixed with 0.25 ml of water, 0.25 ml of m-cresol, 0.25 ml of thioanisole, 0.125 ml of 1,2-ethandithiol and 4.125 ml of trifluoroacetic acid with cooling in ice, and the mixture was stirred at room temperature for 1 hour. Cleaved peptides were precipitated with about a 5-fold volume of ether. The peptides were lyophilized and dissolved in 0.05% trifluoroacetic acid in water. Then, the peptides were purified by high performance liquid chromatography (HPLC) and lyophilized.

EXAMPLE 2

Synthesis of Peptide Trimer Unit by Selective Disulfide Crosslinking

1) Pyridinesulfenylation of M-peptide: Synthesis of M-peptide (Acm, SPy)
25 mg (11.2 µmol) of M-peptide (Acm, SH) was dissolved in 50 mM sodium acetate (pH 5.4) containing 2 mM EDTA [Buffer A], and the solution was mixed with 2,2'-dipyridyldisulfide (49.5 mg, 225 µmol) dissolved in 2-propanol at room temperature under a nitrogen atmosphere to allow the reaction to proceed for 1 hour. The desired produce was purified by HPLC and lyophilized.
2) Synthesis of M-C Dimer (Acm, SS) by Heterodimerization of M-peptide (Acm, SPy) and C-peptide (SH)
13.2 mg (5.66 µmol) of M-peptide (Acm, SPy) was dissolved in 0.66 ml of Buffer A, and the solution was added dropwise to 0.735 ml of Buffer A containing 14.7 mg (6.79 µmol) of C-peptide (SH) at room temperature under a nitrogen atmosphere. The reaction solution was shaded from the sun and stirred for 80 minutes. The desired product was purified by HPLC and lyophilized.
3) Selective S-nitropyridinesulfenylation of M-C dimer (Acm, SS): Synthesis of M-C Dimer (Npys, SS)
10.3 mg (2.35 µmol) of M-C dimer (Acm, SS) was dissolved in 0.412 ml of trifluoroacetic acid:acetic acid (1:2, v/v). 3-Nitro-2-pyridinesulfenyl chloride (1.1 mg, 5.87 µmol) was dissolved in 0.6 ml of trifluoroacetic acid:acetic acid (1:2, v/v) in the same manner, and the solution was added dropwise to the peptide solution at room temperature under a nitrogen atmosphere. The reaction solution was shaded from the sun and stirred for 45 minutes. The desired produce was purified by HPLC and lyophilized.
4) Synthesis of Peptide Trimer Unit by Selective Disulfide Crosslinking Formation Between M-C Dimer (Npys SS) and N-peptide (SH)
3.9 mg (1.81 µmol) of N-peptide (SH) was dissolved in 0.39 ml of Buffer A and added dropwise to 0.81 ml of Buffer A containing 8.1 mg (1.81 µmol) of M-C dimer (Npys, SS) at room temperature under a nitrogen atmosphere. The reaction solution was shaded from the sun and stirred for 90 minutes. The desired produce was purified by HPLC (4.6 id×250 mm) and lyophilized. The synthesized peptide trimer unit was identified by MALDI-TOF MS. Found (M+H)$^+$: 6458. Calculated (M+H)$^+$: 6458.

EXAMPLE 3

Formation of Supramolecule by Self-Assembly

The peptide trimer unit was dissolved in water at a concentration of 10 mg/ml, and the solution was left stand at 4° C. for 14 days (stock solution).
1) Structural Analysis by Measurement of Circular Dichroism Spectrum The stock solution was diluted to 5-fold with water at 4° C. and analyzed for supramolecule formation.

The measurement conditions are as follows:
Device: A JASCO J-820 device equipped with a PTC-423 L temperature control unit
Cell length: 0.5 mm
Measurement wavelength: 210 to 260 nm
Data collection: every 0.2 nm
Scan rate: 50 nm/min
Response: 2 sec
Data integration: 3 times
Sensitivity: 100 mdeg
Measurement temperatures: 4, 30, 40, 50, 60, and 70° C.

Figure 4:
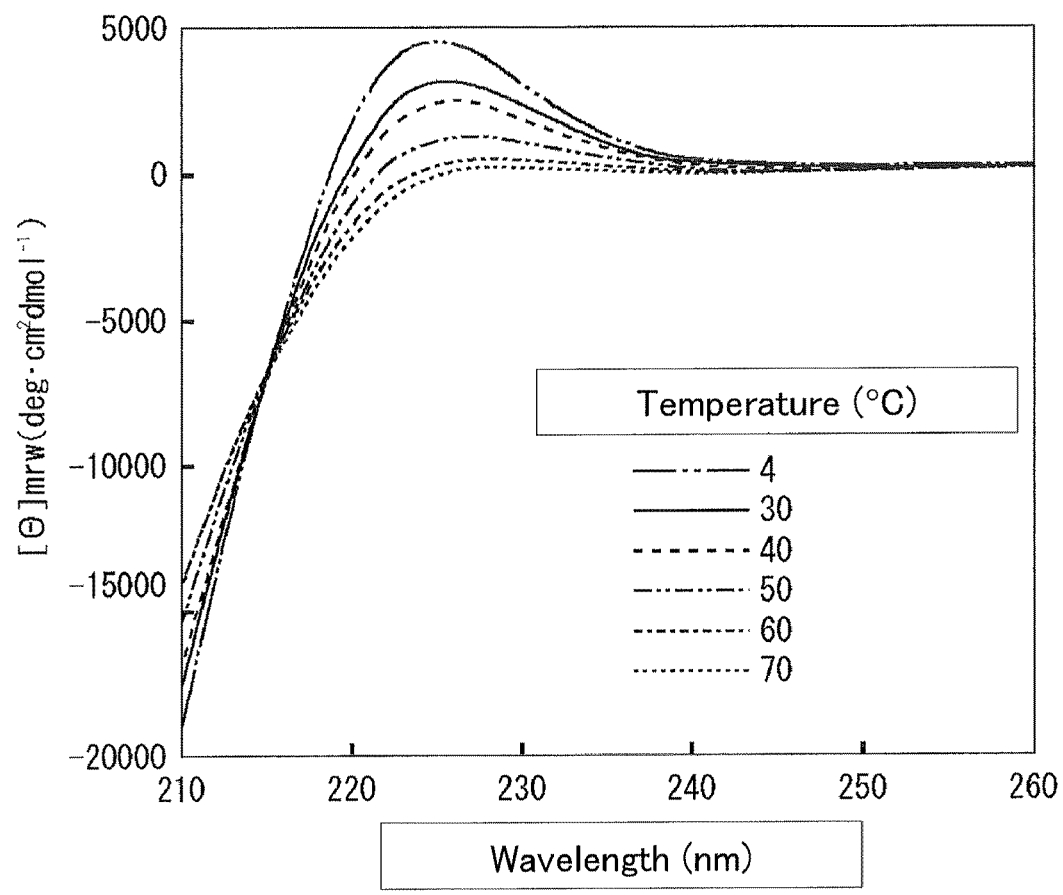
FIG. 4 shows the circular dichroism spectra of a molecular aggregate prepared according to the present invention.

The results are shown in FIG. 4. The spectra of the supramolecule at a lower temperature had a positive signal at 225 nm and showed a typical spectral pattern of the triple helix structure of collagen. Due to the design of the peptide unit, a single molecule of the peptide unit cannot have a triple helix structure. Thus, it is construed that these results shows that triple helix formation (supramolecular formation) occurs among unit molecules. The value of mean residue molar ellipticity ([θ]mrw) at 225 nm of the triple helix of the collagen-like peptide is equal to that of natural collagen, suggesting that the content of triple helix in the supramolecule is very high. The results also showed that the triple helix structure is denatured by heat, resulting in a random coil structure.

2) Analysis of Supramolecule by Ultrafiltration

Figure 5:
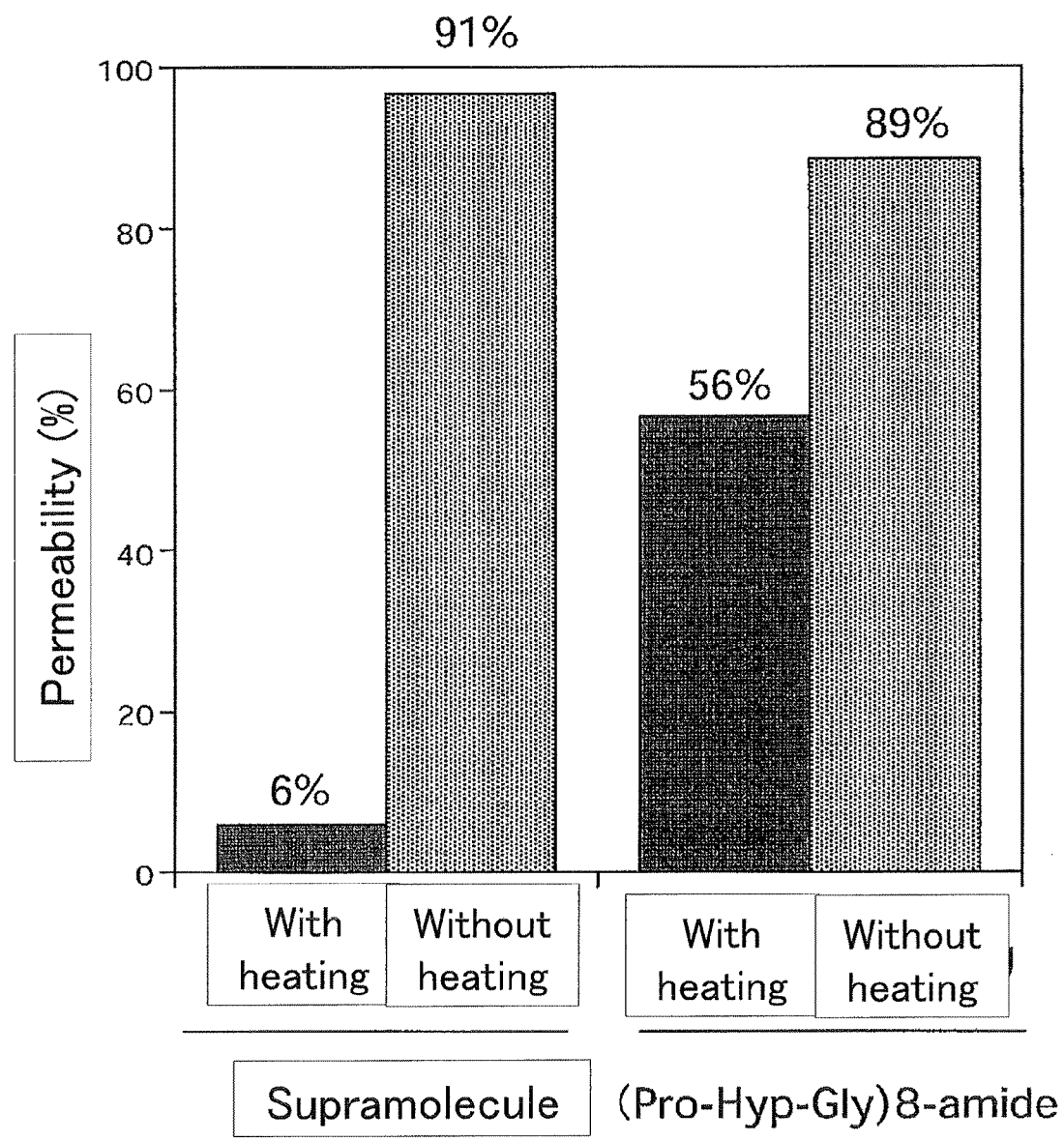
FIG. 5 shows the ultrafiltration membrane permeability of a molecular aggregate prepared according to the present invention.

The stock solution of supramolecule was diluted to 20-fold with water at 4° C. As a control, (Pro-Hyp-Gly)$_8$-amide was left at 4° C. to allow for triple helix formation and diluted with water in the same manner. Then, each diluted solution was subjected to ultrafiltration at 4° C. with Microcon YM-100 (cut-off: 100,000 MW). The filtrate was analyzed by HPLC, and ultrafiltration membrane permeability was calculated from the peak area. The same solution was heated at 95° C. for 5 minutes to denature the triple helix structure and immediately analyzed for the permeability in the same manner. The results are shown in FIG. 5.

A small fraction (6%) of the peptides formed a supramolecule that passed through the ultrafiltration membrane. On the other hand, the (Pro-Hyp-Gly)$_8$-amide having the same peptide chain length and composed of substantially the same amino acid structure, 56% of the peptides passed through the membrane. By subjecting the solution of supramolecule to thermal denaturation, 91% of the peptides could pass through the membrane. These results suggests that a large structure is generated in the solution of supramolecule due to the intermolecular interaction (triple helix formation).

EXAMPLE 4

Synthesis and Characterization of Staggered Trimer

A peptide trimer (staggered trimer) was synthesized which was designed to have a repeat of Pro-Hyp-Gly as a fundamental sequence similar to the peptide trimer unit of Example 1 except that the position of the disulfide crosslink is different. The structure is shown in FIG. 6.

The following three peptides were used as peptide monomers.

H-Hyp-Gly-Pro-Hyp-Gly-Pro-Hyp-Gly-Pro-Hyp-Gly-Pro-Hyp-Gly-Pro-Hyp-Gly-Pro-Cys(SH)-Gly-Pro-Hyp-Gly-Pro-OH (SEQ ID NO: 4)

H-Hyp-Gly-Pro-Hyp-Gly-Cys(Acm)-Hyp-Gly-Pro-Hyp-Gly-Pro-Hyp-Gly-Pro-Hyp-Gly-Pro-Cys(SH)-Gly-Pro-Hyp-Gly-Pro-OH (SEQ ID NO: 5)

H-Hyp-Gly-Pro-Hyp-Gly-Cys(SH)-Hyp-Gly-Pro-Hyp-Gly-Pro-Hyp-Gly-Pro-Hyp-Gly-Pro-Hyp-Gly-Pro-Hyp-Gly-Pro-OH (SEQ ID NO: 6)

The staggered trimer was synthesized by the same method as in Example 1 and identified by mass spectrometry. The staggered trimer was formed into a supramolecule at a low temperature in the same manner as in Example 2. Measurement of the circular dichroism spectra showed that substantially the same results as in Example 2 (FIG. 4) were obtained.

Figure 7:
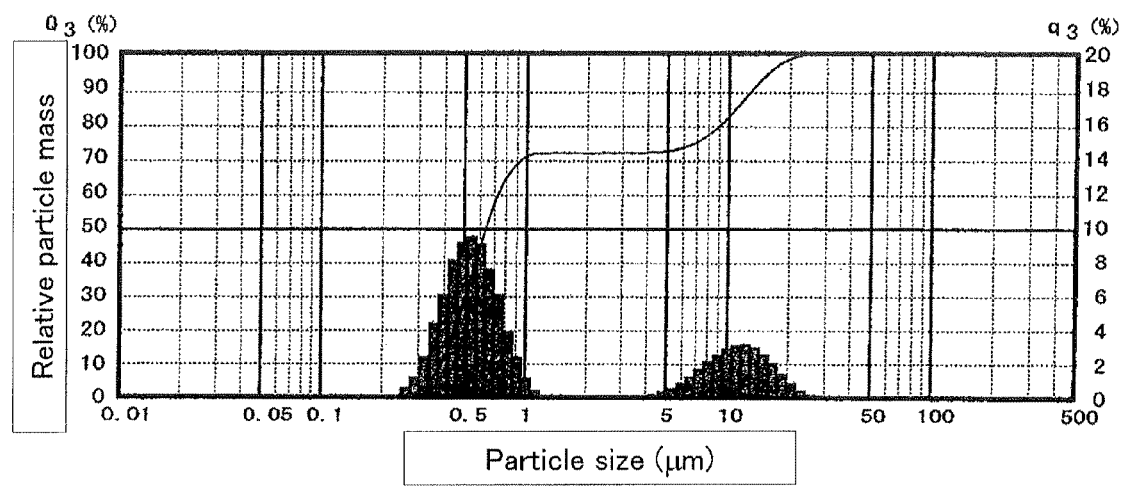
FIG. 7 shows a particle size distribution of a molecular aggregate prepared according to the present invention.

Then, the stock aqueous solution of the staggered trimer (10 mg/ml) was diluted to 12-fold with water at 4° C. and left stand at 4° C. for 1 hour. Then, the particle size distribution was measured with Shimadzu Laser Diffraction Particle Size Distribution Analyzer (SALD-700) at 4° C. and at a laser wavelength of 405 nm. The results are shown in FIG. 7. Supramolecular structures that provide particle sizes of about 0.5 and about 10 μm were detected.

The invention claimed is:

1. A synthetic peptide trimer comprising three peptides of the same chain length, wherein said peptides have the repeating unit of -(-Gly-X-Y-)- as the fundamental structure and X and Y represent any amino acid residue and wherein said peptides are each tethered to one another such that they are shifted relative to one another in the backbone direction, and wherein the peptide trimer has a single-stranded region or a double-stranded region which is longer than a triple-stranded region.

2. The peptide trimer according to claim 1, wherein the three peptides are tethered to one another via a disulfide bond.

3. The peptide trimer according to claim 1 or 2, wherein among the three peptides, two peptides each have one Cys residue and the other one peptide has two Cys residues.

4. The peptide trimer according to claim 1, wherein 30% or more of X is Pro and 30% or more of Y is Pro or Hyp in the whole molecule of the peptide trimer.

5. A method of producing the peptide trimer according to claim 1, comprising the steps of:
 preparing a first peptide having one Cys residue, a second peptide having two Cys residues, one of which has a protected SH group, and a third peptide having one Cys residue;
 forming a peptide dimer by linking the first peptide to the second peptide via a disulfide bond;
 activating the protected SH of the second peptide by converting the protecting group; and
 linking the peptide dimer and the third peptide via a disulfide bond.

6. A molecular aggregate having a triple helix structure comprised of the peptide trimer according to claim 1.

7. A method of producing the molecular aggregate according to claim 6, comprising holding a solution of the peptide trimer according to claim 1 at a temperature between 0 and 40° C. for 1 hour or longer.

8. The synthetic peptide trimer of claim 1 wherein each of the three peptides has a length of 10 to 60 amino acid residues in total.

9. The synthetic peptide trimer of claim 1 wherein each of the three peptides has a length of 15 to 40 amino acid residues in total.

10. The synthetic peptide trimer of claim 1 wherein each of the three peptides has a length of 20 to 30 amino acid residues.

11. The synthetic peptide trimer of claim 1 wherein at least one of the three peptides has the structure H-(Gly-X-Y)$_7$-Gly-Pro-Cys(SH)-OH (SEQ ID NO: 8), wherein X and Y can be any amino acid and SH indicates a disulfide bond.

12. The synthetic peptide trimer of claim 1 wherein at least one of the three peptides has the structure disclosed in any one of SEQ ID NOs: 1-6.

13. The synthetic peptide trimer of claim 1 wherein at least one of the three peptides has the structure H-Hyp-(Gly-X-Y)$_3$-Gly-Cys(Acm)-Cys(SH)-(Gly-X-Y)$_3$-Gly-Pro-OH (SEQ ID NO: 9), wherein X and Y can be any amino acid and SH indicates a disulfide bond.

14. The synthetic peptide trimer of claim 1 wherein at least one of the three peptides has the structure H-Cys(SH)-(Gly-X-Y)$_7$-Hyp-Gly-OH (SEQ ID NO: 10), wherein X and Y can be any amino acid and SH indicates a disulfide bond.

15. The synthetic peptide trimer of claim 1 wherein at least one of the three peptides has the structure H-Hyp-(Gly-X-Y)$_5$-Gly-Pro-Cys(SH)-(Gly-X-Y)$_1$-Gly-Pro-OH (SEQ ID NO: 11), wherein X and Y can be any amino acid and SH indicates a disulfide bond.

16. The synthetic peptide trimer of claim 1 wherein at least one of the three peptides has the structure H-Hyp-(Gly-X-Y)$_1$-Gly-Cys(Acm)-Hyp-(Gly-X-Y)$_3$-Gly-Pro-Cys(SH)-(Gly-X-Y)$_1$-Gly-Pro-OH (SEQ ID NO: 12), wherein X and Y can be any amino acid and SH indicates a disulfide bond.

17. The synthetic peptide trimer of claim 1 wherein at least one of the three peptides has the structure H-Hyp-(Gly-X-Y)$_1$-Gly-Cys(SH)-Hyp-(Gly-X-Y)$_5$-Gly-Pro-OH (SEQ ID NO: 13), wherein X and Y can be any amino acid and SH indicates a disulfide bond.

* * * * *

SEQUENCE LISTING

```
<160> NUMBER OF SEQ ID NOS: 13

<210> SEQ ID NO 1
<211> LENGTH: 24
<212> TYPE: PRT
<213> ORGANISM: Artificial Sequence
<220> FEATURE:
<223> OTHER INFORMATION: Synthetic peptide unit of triplex-forming
      polypeptide
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (9)..(9)
<223> OTHER INFORMATION: 4Hyp
<220> FEATURE:
<221> NAME/KEY: MOD_RES
<222> LOCATION: (12)..(12)
```

```
<223> OTHER INFORMATION: 4Hyp
<220> FEATURE:
<221> NAME/KEY: MOD_RES
<222> LOCATION: (15)..(15)
<223> OTHER INFORMATION: 4Hyp
<220> FEATURE:
<221> NAME/KEY: MOD_RES
<222> LOCATION: (18)..(18)
<223> OTHER INFORMATION: 4Hyp
<220> FEATURE:
<221> NAME/KEY: MOD_RES
<222> LOCATION: (21)..(21)
<223> OTHER INFORMATION: 4Hyp

<400> SEQUENCE: 1

Gly Pro Xaa Gly Pro Xaa Gly Pro Xaa Gly Pro Xaa Gly Pro Xaa Gly
1               5                   10                  15

Pro Xaa Gly Pro Xaa Gly Pro Cys
            20

<210> SEQ ID NO 2
<211> LENGTH: 24
<212> TYPE: PRT
<213> ORGANISM: Artificial Sequence
<220> FEATURE:
<223> OTHER INFORMATION: Synthetic peptide unit of triplex-forming
      polypeptide
<220> FEATURE:
<221> NAME/KEY: MOD_RES
<222> LOCATION: (1)..(1)
<223> OTHER INFORMATION: 4Hyp
<220> FEATURE:
<221> NAME/KEY: MOD_RES
<222> LOCATION: (4)..(4)
<223> OTHER INFORMATION: 4Hyp
<220> FEATURE:
<221> NAME/KEY: MOD_RES
<222> LOCATION: (7)..(7)
<223> OTHER INFORMATION: 4Hyp
<220> FEATURE:
<221> NAME/KEY: MOD_RES
<222> LOCATION: (10)..(10)
<223> OTHER INFORMATION: 4Hyp
<220> FEATURE:
<221> NAME/KEY: MOD_RES
<222> LOCATION: (16)..(16)
<223> OTHER INFORMATION: 4Hyp
<220> FEATURE:
<221> NAME/KEY: MOD_RES
<222> LOCATION: (19)..(19)
<223> OTHER INFORMATION: 4Hyp
<220> FEATURE:
<221> NAME/KEY: MOD_RES
<222> LOCATION: (22)..(22)
<223> OTHER INFORMATION: 4Hyp

<400> SEQUENCE: 2

Xaa Gly Pro Xaa Gly Pro Xaa Gly Pro Xaa Gly Cys Cys Gly Pro Xaa
1               5                   10                  15

Gly Pro Xaa Gly Pro Xaa Gly Pro
            20

<210> SEQ ID NO 3
<211> LENGTH: 24
<212> TYPE: PRT
<213> ORGANISM: Artificial Sequence
<220> FEATURE:
<223> OTHER INFORMATION: Synthetic peptide unit of triplex-forming
      polypeptide
<220> FEATURE:
<221> NAME/KEY: MOD_RES
<222> LOCATION: (2)..(2)
<223> OTHER INFORMATION: 4Hyp
<220> FEATURE:
```

```
<221> NAME/KEY: MOD_RES
<222> LOCATION: (5)..(5)
<223> OTHER INFORMATION: 4Hyp
<220> FEATURE:
<221> NAME/KEY: MOD_RES
<222> LOCATION: (8)..(8)
<223> OTHER INFORMATION: 4Hyp
<220> FEATURE:
<221> NAME/KEY: MOD_RES
<222> LOCATION: (11)..(11)
<223> OTHER INFORMATION: 4Hyp
<220> FEATURE:
<221> NAME/KEY: MOD_RES
<222> LOCATION: (14)..(14)
<223> OTHER INFORMATION: 4Hyp
<220> FEATURE:
<221> NAME/KEY: MOD_RES
<222> LOCATION: (17)..(17)
<223> OTHER INFORMATION: 4Hyp
<220> FEATURE:
<221> NAME/KEY: MOD_RES
<222> LOCATION: (20)..(20)
<223> OTHER INFORMATION: 4Hyp
<220> FEATURE:
<221> NAME/KEY: MOD_RES
<222> LOCATION: (23)..(23)
<223> OTHER INFORMATION: 4Hyp

<400> SEQUENCE: 3

Cys Xaa Gly Pro Xaa Gly Pro Xaa Gly Pro Xaa Gly Pro Xaa Gly Pro
1               5                   10                  15

Xaa Gly Pro Xaa Gly Pro Xaa Gly
            20

<210> SEQ ID NO 4
<211> LENGTH: 24
<212> TYPE: PRT
<213> ORGANISM: Artificial Sequence
<220> FEATURE:
<223> OTHER INFORMATION: Synthetic peptide unit of triplex-forming
      polypeptide
<220> FEATURE:
<221> NAME/KEY: MOD_RES
<222> LOCATION: (1)..(1)
<223> OTHER INFORMATION: 4Hyp
<220> FEATURE:
<221> NAME/KEY: MOD_RES
<222> LOCATION: (4)..(4)
<223> OTHER INFORMATION: 4Hyp
<220> FEATURE:
<221> NAME/KEY: MOD_RES
<222> LOCATION: (7)..(7)
<223> OTHER INFORMATION: 4Hyp
<220> FEATURE:
<221> NAME/KEY: MOD_RES
<222> LOCATION: (10)..(10)
<223> OTHER INFORMATION: 4Hyp
<220> FEATURE:
<221> NAME/KEY: MOD_RES
<222> LOCATION: (13)..(13)
<223> OTHER INFORMATION: 4Hyp
<220> FEATURE:
<221> NAME/KEY: MOD_RES
<222> LOCATION: (16)..(16)
<223> OTHER INFORMATION: 4Hyp
<220> FEATURE:
<221> NAME/KEY: MOD_RES
<222> LOCATION: (22)..(22)
<223> OTHER INFORMATION: 4Hyp

<400> SEQUENCE: 4

Xaa Gly Pro Xaa Gly Pro Xaa Gly Pro Xaa Gly Pro Xaa Gly Pro Xaa
1               5                   10                  15

Gly Pro Cys Gly Pro Xaa Gly Pro
            20
```

```
<210> SEQ ID NO 5
<211> LENGTH: 24
<212> TYPE: PRT
<213> ORGANISM: Artificial Sequence
<220> FEATURE:
<223> OTHER INFORMATION: Synthetic peptide unit of triplex-forming
      polypeptide
<220> FEATURE:
<221> NAME/KEY: MOD_RES
<222> LOCATION: (1)..(1)
<223> OTHER INFORMATION: 4Hyp
<220> FEATURE:
<221> NAME/KEY: MOD_RES
<222> LOCATION: (4)..(4)
<223> OTHER INFORMATION: 4Hyp
<220> FEATURE:
<221> NAME/KEY: MOD_RES
<222> LOCATION: (7)..(7)
<223> OTHER INFORMATION: 4Hyp
<220> FEATURE:
<221> NAME/KEY: MOD_RES
<222> LOCATION: (10)..(10)
<223> OTHER INFORMATION: 4Hyp
<220> FEATURE:
<221> NAME/KEY: MOD_RES
<222> LOCATION: (13)..(13)
<223> OTHER INFORMATION: 4Hyp
<220> FEATURE:
<221> NAME/KEY: MOD_RES
<222> LOCATION: (16)..(16)
<223> OTHER INFORMATION: 4Hyp
<220> FEATURE:
<221> NAME/KEY: MOD_RES
<222> LOCATION: (22)..(22)
<223> OTHER INFORMATION: 4Hyp

<400> SEQUENCE: 5

Xaa Gly Pro Xaa Gly Cys Xaa Gly Pro Xaa Gly Pro Xaa Gly Pro Xaa
1               5                   10                  15

Gly Pro Cys Gly Pro Xaa Gly Pro
            20

<210> SEQ ID NO 6
<211> LENGTH: 24
<212> TYPE: PRT
<213> ORGANISM: Artificial Sequence
<220> FEATURE:
<223> OTHER INFORMATION: Synthetic peptide unit of triplex-forming
      polypeptide
<220> FEATURE:
<221> NAME/KEY: MOD_RES
<222> LOCATION: (1)..(1)
<223> OTHER INFORMATION: 4Hyp
<220> FEATURE:
<221> NAME/KEY: MOD_RES
<222> LOCATION: (4)..(4)
<223> OTHER INFORMATION: 4Hyp
<220> FEATURE:
<221> NAME/KEY: MOD_RES
<222> LOCATION: (7)..(7)
<223> OTHER INFORMATION: 4Hyp
<220> FEATURE:
<221> NAME/KEY: MOD_RES
<222> LOCATION: (10)..(10)
<223> OTHER INFORMATION: 4Hyp
<220> FEATURE:
<221> NAME/KEY: MOD_RES
<222> LOCATION: (13)..(13)
<223> OTHER INFORMATION: 4Hyp
<220> FEATURE:
<221> NAME/KEY: MOD_RES
<222> LOCATION: (16)..(16)
<223> OTHER INFORMATION: 4Hyp
<220> FEATURE:
<221> NAME/KEY: MOD_RES
```

-continued

```
<222> LOCATION: (19)..(19)
<223> OTHER INFORMATION: 4Hyp
<220> FEATURE:
<221> NAME/KEY: MOD_RES
<222> LOCATION: (22)..(22)
<223> OTHER INFORMATION: 4Hyp

<400> SEQUENCE: 6

Xaa Gly Pro Xaa Gly Cys Xaa Gly Pro Xaa Gly Pro Xaa Gly Pro Xaa
1               5                   10                  15

Gly Pro Xaa Gly Pro Xaa Gly Pro
            20

<210> SEQ ID NO 7
<211> LENGTH: 46
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: MOD_RES
<222> LOCATION: (8)..(8)
<223> OTHER INFORMATION: 4Hyp
<220> FEATURE:
<221> NAME/KEY: MOD_RES
<222> LOCATION: (11)..(11)
<223> OTHER INFORMATION: 4Hyp
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: MOD_RES
<222> LOCATION: (14)..(14)
<223> OTHER INFORMATION: 4Hyp
<220> FEATURE:
<221> NAME/KEY: MOD_RES
<222> LOCATION: (17)..(17)
<223> OTHER INFORMATION: 4Hyp
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: MOD_RES
<222> LOCATION: (20)..(20)
<223> OTHER INFORMATION: 4Hyp
<220> FEATURE:
<221> NAME/KEY: MOD_RES
<222> LOCATION: (23)..(23)
<223> OTHER INFORMATION: 4Hyp
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: MOD_RES
<222> LOCATION: (26)..(26)
<223> OTHER INFORMATION: 4Hyp
<220> FEATURE:
<221> NAME/KEY: MOD_RES
<222> LOCATION: (29)..(29)
<223> OTHER INFORMATION: 4Hyp
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: MOD_RES
<222> LOCATION: (32)..(32)
<223> OTHER INFORMATION: 4Hyp
<220> FEATURE:
<221> NAME/KEY: MOD_RES
```

```
<222> LOCATION: (35)..(35)
<223> OTHER INFORMATION: 4Hyp
<220> FEATURE:
<221> NAME/KEY: misc_feature
<222> LOCATION: (37)..(37)
<223> OTHER INFORMATION: Xaa can be any naturally occurring amino acid
<220> FEATURE:
<221> NAME/KEY: MOD_RES
<222> LOCATION: (38)..(38)
<223> OTHER INFORMATION: 4Hyp
<220> FEATURE:
<221> NAME/KEY: MOD_RES
<222> LOCATION: (41)..(41)
<223> OTHER INFORMATION: 4Hyp

<400> SEQUENCE: 7

Glu Glu Glu Glu Glu Gly Xaa Xaa Gly Pro Xaa Gly Xaa Xaa Gly Pro
1               5                   10                  15

Xaa Gly Xaa Xaa Gly Pro Xaa Gly Xaa Xaa Gly Pro Xaa Gly Xaa Xaa
            20                  25                  30

Gly Pro Xaa Gly Xaa Xaa Gly Pro Xaa Glu Glu Glu Glu Glu
        35                  40                  45

<210> SEQ ID NO 8
<211> LENGTH: 24
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid
<220> FEATURE:
<221> NAME/KEY: misc_feature
<222> LOCATION: (17)..(18)
<223> OTHER INFORMATION: Xaa can be any naturally occurring amino acid
<220> FEATURE:
<221> NAME/KEY: misc_feature
<222> LOCATION: (20)..(21)
<223> OTHER INFORMATION: Xaa can be any naturally occurring amino acid

<400> SEQUENCE: 8

Gly Xaa Xaa Gly Xaa Xaa Gly Xaa Xaa Gly Xaa Xaa Gly Xaa Xaa Gly
1               5                   10                  15

Xaa Xaa Gly Xaa Xaa Gly Pro Cys
            20

<210> SEQ ID NO 9
<211> LENGTH: 24
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
```

-continued

```
<223> OTHER INFORMATION: 4Hyp
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
<222> LOCATION: (15)..(16)
<223> OTHER INFORMATION: Xaa can be any naturally occurring amino acid
<220> FEATURE:
<221> NAME/KEY: misc_feature
<222> LOCATION: (18)..(19)
<223> OTHER INFORMATION: Xaa can be any naturally occurring amino acid
<220> FEATURE:
<221> NAME/KEY: misc_feature
<222> LOCATION: (21)..(22)
<223> OTHER INFORMATION: Xaa can be any naturally occurring amino acid

<400> SEQUENCE: 9

Xaa Gly Xaa Xaa Gly Xaa Xaa Gly Xaa Xaa Gly Cys Cys Gly Xaa Xaa
1               5                   10                  15

Gly Xaa Xaa Gly Xaa Xaa Gly Pro
            20

<210> SEQ ID NO 10
<211> LENGTH: 24
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
<222> LOCATION: (12)..(13)
<223> OTHER INFORMATION: Xaa can be any naturally occurring amino acid
<220> FEATURE:
<221> NAME/KEY: misc_feature
<222> LOCATION: (15)..(16)
<223> OTHER INFORMATION: Xaa can be any naturally occurring amino acid
<220> FEATURE:
<221> NAME/KEY: misc_feature
<222> LOCATION: (18)..(19)
<223> OTHER INFORMATION: Xaa can be any naturally occurring amino acid
<220> FEATURE:
<221> NAME/KEY: misc_feature
<222> LOCATION: (21)..(22)
<223> OTHER INFORMATION: Xaa can be any naturally occurring amino acid
<220> FEATURE:
<221> NAME/KEY: MOD_RES
<222> LOCATION: (23)..(23)
<223> OTHER INFORMATION: 4Hyp

<400> SEQUENCE: 10

Cys Gly Xaa Xaa Gly Xaa Xaa Gly Xaa Xaa Gly Xaa Xaa Gly Xaa Xaa
1               5                   10                  15

Gly Xaa Xaa Gly Xaa Xaa Xaa Gly
```

-continued

```
<210> SEQ ID NO 11
<211> LENGTH: 24
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: 4Hyp
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
<222> LOCATION: (12)..(13)
<223> OTHER INFORMATION: Xaa can be any naturally occurring amino acid
<220> FEATURE:
<221> NAME/KEY: misc_feature
<222> LOCATION: (15)..(16)
<223> OTHER INFORMATION: Xaa can be any naturally occurring amino acid
<220> FEATURE:
<221> NAME/KEY: misc_feature
<222> LOCATION: (21)..(22)
<223> OTHER INFORMATION: Xaa can be any naturally occurring amino acid

<400> SEQUENCE: 11

Xaa Gly Xaa Xaa Gly Xaa Xaa Gly Xaa Xaa Gly Xaa Xaa Gly Xaa Xaa
1               5                   10                  15

Gly Pro Cys Gly Xaa Xaa Gly Pro
            20

<210> SEQ ID NO 12
<211> LENGTH: 24
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: 4Hyp
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: MOD_RES
<222> LOCATION: (7)..(7)
<223> OTHER INFORMATION: 4Hyp
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
<222> LOCATION: (12)..(13)
<223> OTHER INFORMATION: Xaa can be any naturally occurring amino acid
<220> FEATURE:
<221> NAME/KEY: misc_feature
<222> LOCATION: (15)..(16)
<223> OTHER INFORMATION: Xaa can be any naturally occurring amino acid
<220> FEATURE:
<221> NAME/KEY: misc_feature
<222> LOCATION: (21)..(22)
```

-continued

```
<223> OTHER INFORMATION: Xaa can be any naturally occurring amino acid

<400> SEQUENCE: 12

Xaa Gly Xaa Xaa Gly Cys Xaa Gly Xaa Xaa Gly Xaa Xaa Gly Xaa Xaa
1               5                   10                  15

Gly Pro Cys Gly Xaa Xaa Gly Pro
            20

<210> SEQ ID NO 13
<211> LENGTH: 24
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: 4Hyp
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: MOD_RES
<222> LOCATION: (7)..(7)
<223> OTHER INFORMATION: 4Hyp
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
<222> LOCATION: (12)..(13)
<223> OTHER INFORMATION: Xaa can be any naturally occurring amino acid
<220> FEATURE:
<221> NAME/KEY: misc_feature
<222> LOCATION: (15)..(16)
<223> OTHER INFORMATION: Xaa can be any naturally occurring amino acid
<220> FEATURE:
<221> NAME/KEY: misc_feature
<222> LOCATION: (18)..(19)
<223> OTHER INFORMATION: Xaa can be any naturally occurring amino acid
<220> FEATURE:
<221> NAME/KEY: misc_feature
<222> LOCATION: (21)..(22)
<223> OTHER INFORMATION: Xaa can be any naturally occurring amino acid

<400> SEQUENCE: 13

Xaa Gly Xaa Xaa Gly Cys Xaa Gly Xaa Xaa Gly Xaa Xaa Gly Xaa Xaa
1               5                   10                  15

Gly Xaa Xaa Gly Xaa Xaa Gly Pro
            20
```